US008609041B2

(12) United States Patent
Mitragotri et al.

(10) Patent No.: US 8,609,041 B2
(45) Date of Patent: Dec. 17, 2013

(54) APPARATUS FOR SOLUBILIZING TISSUE

(76) Inventors: Samir Mitragotri, Santa Barbara, CA (US); Sumit Paliwal, Goleta, CA (US); Makoto Ogura, Ryugasaki (JP); Russell M. Lebovitz, San Diego, CA (US); MyPhuong Lam, Houston, TX (US)

( * ) Notice: Subject to any disclaimer, the term of this patent is extended or adjusted under 35 U.S.C. 154(b) by 153 days.

(21) Appl. No.: 13/095,771

(22) Filed: Apr. 27, 2011

(65) Prior Publication Data
US 2011/0295149 A1 Dec. 1, 2011

Related U.S. Application Data

(63) Continuation-in-part of application No. 12/664,994, filed as application No. PCT/US2008/072384 on Aug. 6, 2008, application No. 13/095,771, which is a continuation-in-part of application No. 13/126,105, filed as application No. PCT/US2010/024010 on Feb. 12, 2010.

(60) Provisional application No. 60/963,773, filed on Aug. 6, 2007, provisional application No. 61/152,285, filed on Feb. 13, 2009.

(51) Int. Cl.
*A61B 10/00* (2006.01)

(52) U.S. Cl.
USPC ............. 422/536; 422/63; 422/64; 422/65; 422/66; 422/67; 436/180

(58) Field of Classification Search
USPC .................. 422/63–67, 536; 436/180
See application file for complete search history.

(56) References Cited

U.S. PATENT DOCUMENTS

| 4,268,613 | A | 5/1981 | Okishi |
|---|---|---|---|
| 5,398,690 | A | 3/1995 | Batten et al. |
| 5,492,126 | A | 2/1996 | Hennige et al. |
| 5,696,069 | A | 12/1997 | Ito et al. |
| 5,739,432 | A | 4/1998 | Sinha |
| 5,804,452 | A | 9/1998 | Pronovost et al. |
| 5,913,833 | A | 6/1999 | Elstrom et al. |
| 6,007,497 | A | 12/1999 | Huitema |
| 6,093,551 | A | 7/2000 | Raithel et al. |
| 6,328,728 | B1 | 12/2001 | Holladay et al. |
| 6,544,211 | B1 | 4/2003 | Andrew et al. |
| 6,560,478 | B1 | 5/2003 | Alfano et al. |
| 6,589,173 | B1 | 7/2003 | Mitragotri |
| 2002/0082518 | A1* | 6/2002 | Weiss et al. .......... 600/566 |
| 2003/0060818 | A1 | 3/2003 | Kannenberg et al. |

(Continued)

OTHER PUBLICATIONS

Tutulan-Cunita et al., "Mutational analysis of the yeast multidrug resistance ABC transporter Pdr5p with altered drug specificity", Genes to cells (2005) vol. 10, pp. 409-420.
Pubchem polidocanol (pubchem.ncbi.nlm.nih.gov/summary/summary.cgi?cid=24750&loc=ec_rcs, downloaded Oct. 29, 2012.
Huang et al., "Separation and measurement of desmosine and isodesmosine in vascular tissue hydrolysates by micellar electrokinetic capillary chromatography with a mixed micelle system", J. Chromaography A 1175: 294-296 (2007).

(Continued)

*Primary Examiner* — Jyoti Nagpaul
(74) *Attorney, Agent, or Firm* — Benjamen E. Kern

(57) ABSTRACT

Tissue solubilizing apparatuses are provided. The apparatuses may be useful to solubilize tissue, including skin, mucosal membrane, and other tissue. The apparatuses may be further useful to preserve and recover analytes contained within the solubilized skin, mucosal membrane, and other tissue.

8 Claims, 11 Drawing Sheets

(56) References Cited

U.S. PATENT DOCUMENTS

| | | |
|---|---|---|
| 2003/0143116 A1 | 7/2003 | Zheng et al. |
| 2003/0211520 A1 | 11/2003 | Afar et al. |
| 2004/0151745 A1 | 8/2004 | Zimmer et al. |
| 2005/0164903 A1 | 7/2005 | Ko et al. |
| 2006/0100569 A1 | 5/2006 | McRury et al. |
| 2007/0055181 A1 | 3/2007 | Deem et al. |
| 2007/0055261 A1 | 3/2007 | Reiley et al. |
| 2007/0059687 A1 | 3/2007 | Ohno et al. |
| 2007/0173448 A1 | 7/2007 | Shah et al. |
| 2010/0261176 A1 | 10/2010 | Mitragotri et al. |

OTHER PUBLICATIONS

Written Opinion and International Search Report of the International Searching Authority from related PCT Application No. PCT/US08/72384.

\* cited by examiner

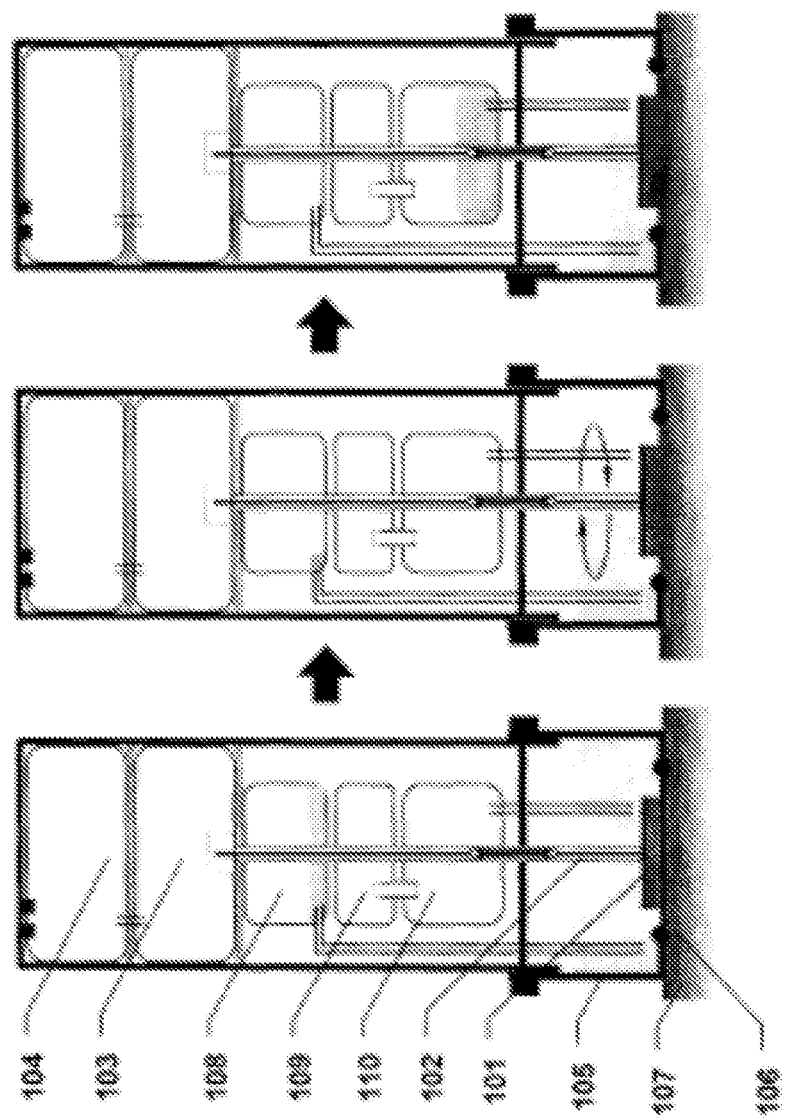

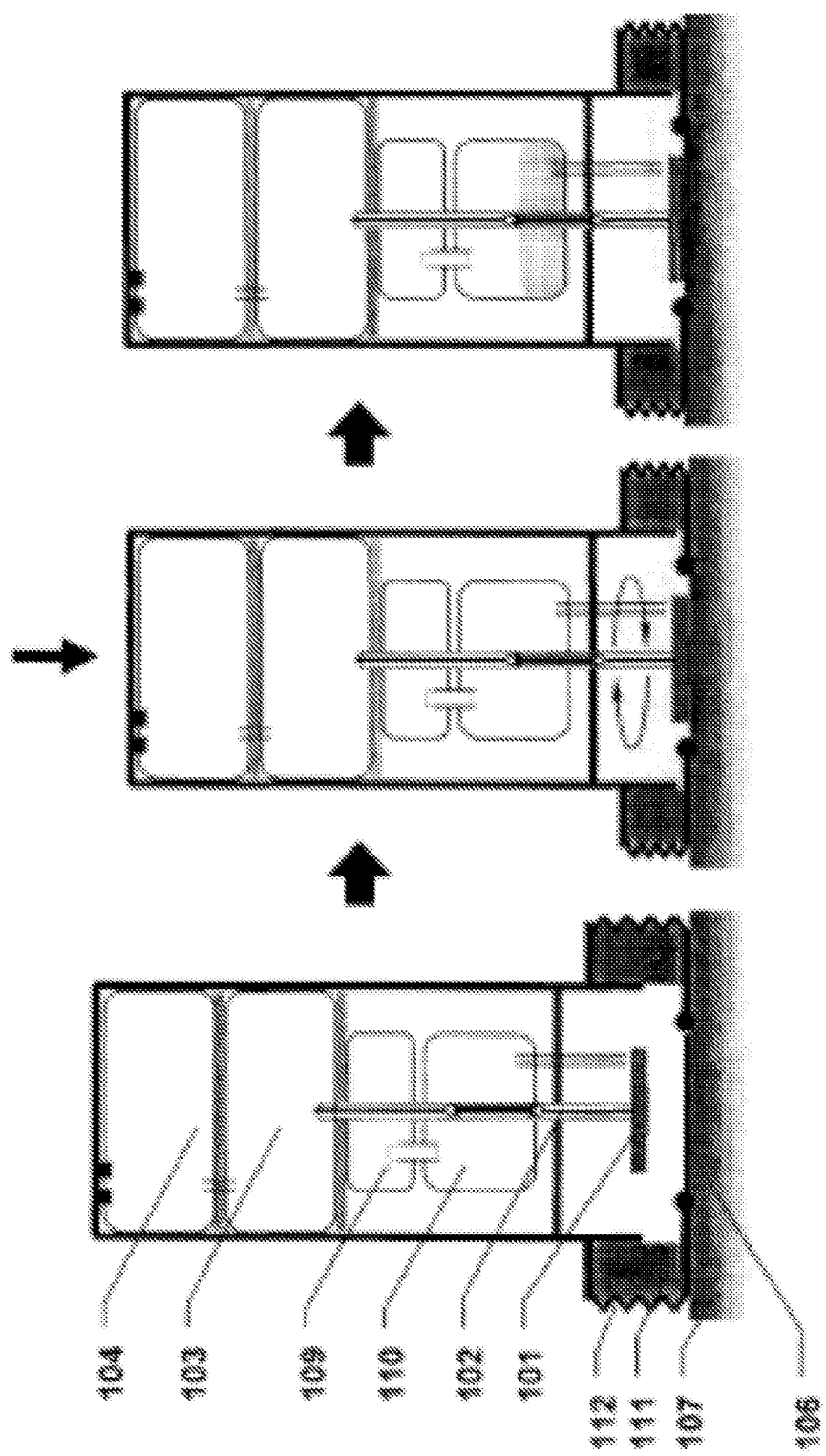

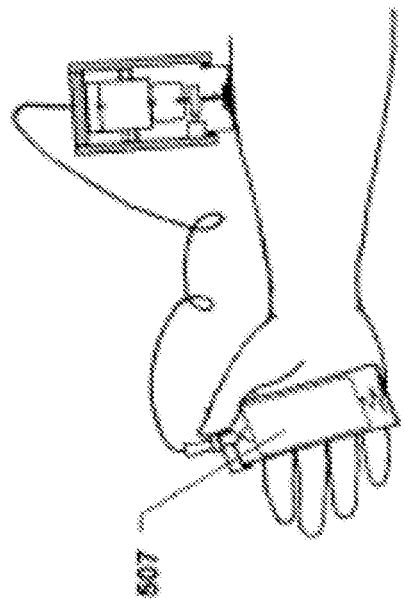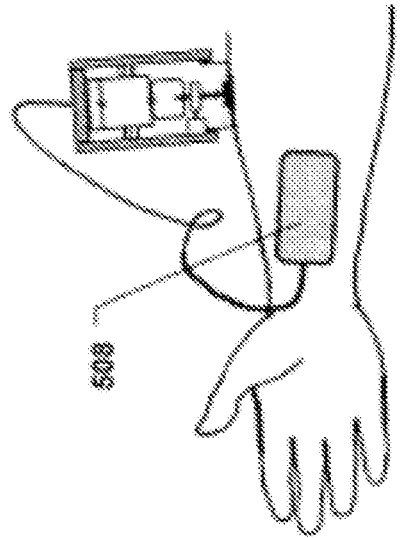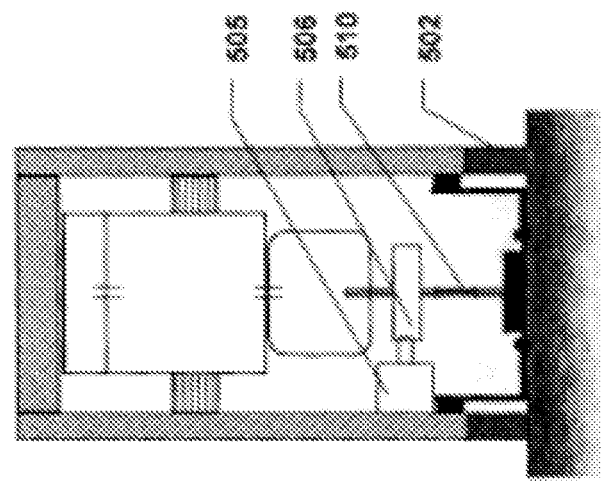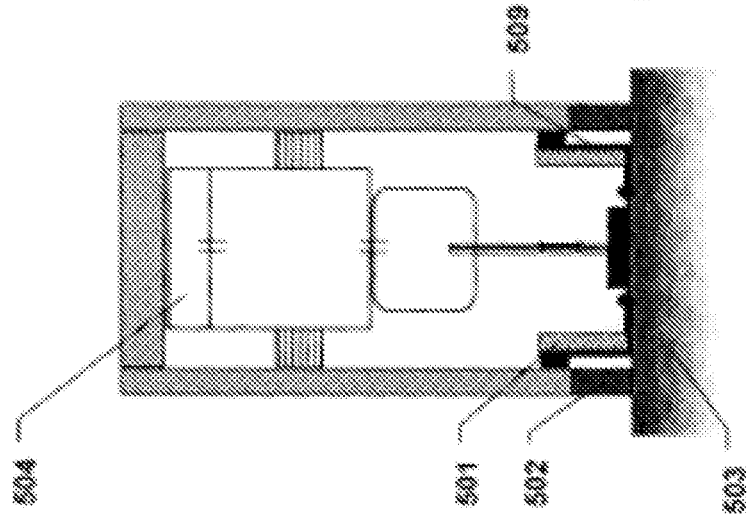

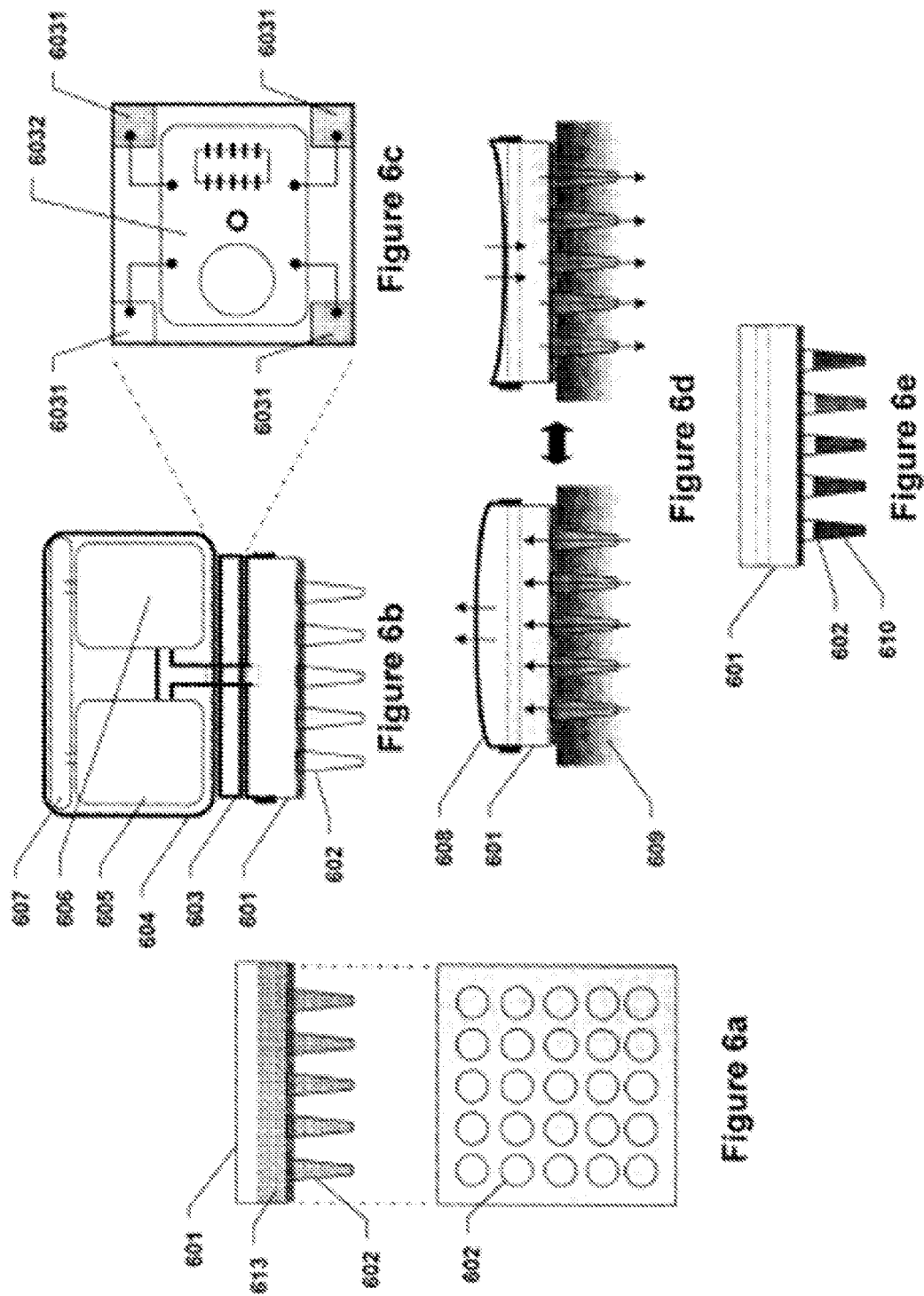

APPARATUS FOR SOLUBILIZING TISSUE

CROSS-REFERENCE TO RELATED APPLICATIONS

This application is a continuation-in-part application of U.S. patent application Ser. No. 12/664,994, filed on Jun. 29, 2010 as a U.S. National Stage filing of PCT/US2008/72384, filed on Aug. 6, 2008, which, in turn, claims priority to U.S. Provisional Patent Application Ser. No. 60/963,773, filed on Aug. 6, 2007, and now expired. This application is also a continuation-in-part application of Ser. No. 13/126,105, filed on Apr. 26, 2011 as a U.S. National Stage filing of PCT/US2010/24010, filed on Feb. 12, 2010, which, in turn, claims priority to U.S. Provisional Patent Application Ser. No. 61/152,285, filed on Feb. 13, 2009, and now expired. All of these related applications are incorporated by reference herein in their entireties.

STATEMENT REGARDING FEDERALLY SPONSORED RESEARCH OR DEVELOPMENT

This invention was made with government support under federal grant number W81XWH-06-01-00400 awarded by the United States Army. The United States Government has certain rights in this invention.

BACKGROUND

Skin is the "window" to the body. Skin is unique among the body's organs for several reasons: (1) skin is the largest organ of the human body; (2) skin is directly exposed to the environment; (3) skin is an excellent excretory organ; (4) skin is the most visible and accessible organ of the body; and (5) skin is a highly active immune organ of the body.

Skin has another important quality: The molecular profile of skin has information that is valuable for physiological monitoring of, among other things, small organic molecules, proteins, DNA, RNA, and lipids. Much can be learned from skin's molecular profiling. For example, pathogens (e.g., bacteria) that grow on skin may allow for forensic identification. Skin's molecular profile may reveal environmental factors to which the body has been passively exposed. These environmental factors may range from the mundane, e.g., allergens, toxins, and cosmetic products, to the industrial and/or agricultural, e.g., industrial solvents, fertilizers, and pesticides, to the dangerous, e.g., explosives and other warfare agents.

Skin's molecular profile may also reveal factors to which the body has been actively exposed. More particularly, skin's molecular profile may reveal what the body has consumed. For example, abused substances (e.g., illegal drugs or narcotics) and therapeutic drugs (e.g., tramadol, fluconazole, barbitals, and anabolic steroids) may be found in skin weeks after consumption.

Skin's molecular profile may also aid diagnosis of conditions and diseases. For example, skin cholesterol is a proxy of the extent of arterial blocks. Glycation of skin collagen is an indicator of a history of diabetes. Skin deposition of β-amyloids may indicate the existence and extent of Alzheimer's disease. And skin globular proteins (e.g., IgE) may indicate allergies to specific allergens.

Several methods exist for sampling biomolecules from skin. For example, one current method is skin biopsy. However, skin biopsy is invasive and analysis is difficult. Practically speaking, skin biopsy is designed for well-equipped experts and, thus, its use in a point-of-care setting is limited. Another current method for sampling biomolecules from skin, tape stripping, suffers from these same limitations and is generally unacceptable because of variability in results. Yet another current method for sampling biomolecules from skin is taking a skin swab. While desirable because of its simplicity, a skin swab is superficial in its depth of inspection, and qualitative in its results. Finally, tissue has been subjected to ultrasound in the presence of surfactants. See U.S. Pat. No. 6,589,173 issued to Mitragotri et al.

Along with providing a cornucopia of information, skin and other epithelial surfaces in the body such as mucosal membranes lining the oral cavity, upper and lower respiratory tracts, upper and lower GI tracts, GU tracts, and cornea of the eye, can also be a host to myriad undesirable cosmetic conditions, such as age spots, skin tags, seborrheic keratosis, scar tissues, xanthomas, non-cancerous hyperproliferative conditions, surface bumps, and scaly patches; and therapeutic conditions such as basal cell and squamous carcinoma skin tumors, and actinic keratosis. Similarly mucosal membranes in the body may be host to surface-located therapeutic conditions such as leukoplakia, and surface cancers relating to Barrett's esophagus and right-colon pre-cancer plaque. For these conditions, solubilization and remodeling or removal may be the primary concern, with or without subsequent diagnostic processing.

Thus, a need exists for an apparatus for skin sampling, as well as for mucosal membrane and other tissue sampling, which at least partially solubilizes such skin, mucosal membrane, and other tissue. A further need exists to preserve the functionality and structural integrity of analytes, including biomolecules, obtained from the solubilized skin, mucosal membrane, and other tissue. Finally, a related need exists for an apparatus to remove surface lesions from skin and mucosal membranes, while preserving biomolecules obtained from the lesions for diagnosis or prognosis.

SUMMARY

In one embodiment, an apparatus for solubilizing tissue is provided, the apparatus comprising: a housing comprising a vacuum chamber and a passage, wherein the vacuum chamber comprises an outer wall, an inner wall, an upper wall, and an interior, and wherein the outer wall, inner wall, and upper wall define the interior, and wherein the inner wall is radially inward of the outer wall. In one embodiment, the vacuum chamber is configured to selectively generate an air pressure within the interior that is less than ambient air pressure and the interior is configured to be operatively connected to the tissue. In another embodiment, the passage is configured to be operatively connected to the tissue. In another embodiment, the apparatus further comprises an energy source configured to be operatively connected to the tissue and configured to access the tissue through the passage. In yet another embodiment, the apparatus further comprises a reservoir configured to contain a liquefaction promoting medium.

In another embodiment, an apparatus for obtaining a solubilized sample from tissue is provided, the apparatus comprising: an energy source configured to be operatively connected to the tissue wherein the energy source is not a heated liquid; a reservoir housing configured to be operatively connected to the tissue, wherein the reservoir housing is configured to apply a liquefaction promoting medium to the tissue.

In another embodiment, an apparatus for obtaining a solubilized sample from tissue is provided, the apparatus comprising: an energy source configured to be operatively connected to the tissue, wherein the energy source is configured to apply a mechanical energy to the tissue; and a reservoir housing configured to be operatively connected to the tissue and configured to contain a liquefaction promoting medium.

In still another embodiment, an apparatus for delivering a drug to a tissue is provided, the apparatus comprising: an energy source configured to be operatively connected to the tissue; a reservoir housing configured to be operatively connected to the tissue and configured to contain a liquefaction promoting medium; and a drug. In another embodiment, the reservoir housing is configured to apply to the tissue at least one of: the liquefaction promoting medium and the drug.

BRIEF DESCRIPTION OF THE DRAWINGS

The accompanying figures, which are incorporated in and constitute a part of the specification, illustrate various example systems, methods, and results, and are used merely to illustrate various example embodiments. It should be noted that various components depicted in the figures may not be drawn to scale, and that the angles and interferences depicted in the figures are presented for purposes of illustration only, and should not be considered in any way as limiting. Corresponding reference characters indicate corresponding parts throughout the several views.

FIG. 1a illustrates a first view of a sequential working of an example embodiment of an apparatus for solubilizing tissue.

FIG. 1b illustrates a second view of a sequential working of an example embodiment of an apparatus for solubilizing tissue.

FIG. 1c illustrates a third view of a sequential working of an example embodiment of an apparatus for solubilizing tissue.

FIG. 1d illustrates an example embodiment of a support shaft component of an energy source for use in an apparatus for solubilizing tissue.

FIG. 1e illustrates a first view of a sequential working of an example embodiment of an apparatus for solubilizing tissue.

FIG. 1f illustrates a second view of a sequential working of an example embodiment of an apparatus for solubilizing tissue.

FIG. 1g illustrates a third view of a sequential working of an example embodiment of an apparatus for solubilizing tissue.

FIG. 5a illustrates an example embodiment of a device for measuring the electrical conductivity of a tissue.

FIG. 5b illustrates an example embodiment of a device for measuring the electrical conductivity of a tissue.

FIG. 5c illustrates an example embodiment of a device for measuring the electrical conductivity of a tissue.

FIG. 5d illustrates an example embodiment of a device for measuring the electrical conductivity of a tissue.

FIG. 6a illustrates an example embodiment of a microneedle-based component of an energy source for use in an apparatus for solubilizing tissue.

FIG. 6b illustrates an example embodiment of a microneedle-based component of an energy source for use in an apparatus for solubilizing tissue.

FIG. 6c illustrates an example embodiment of a microneedle-based component of an energy source for use in an apparatus for solubilizing tissue.

FIG. 6d illustrates an example embodiment of a microneedle-based component of an energy source for use in an apparatus for solubilizing tissue.

FIG. 6e illustrates an example embodiment of a microneedle-based component of an energy source for use in an apparatus for solubilizing tissue.

DETAILED DESCRIPTION

Figure 2B:
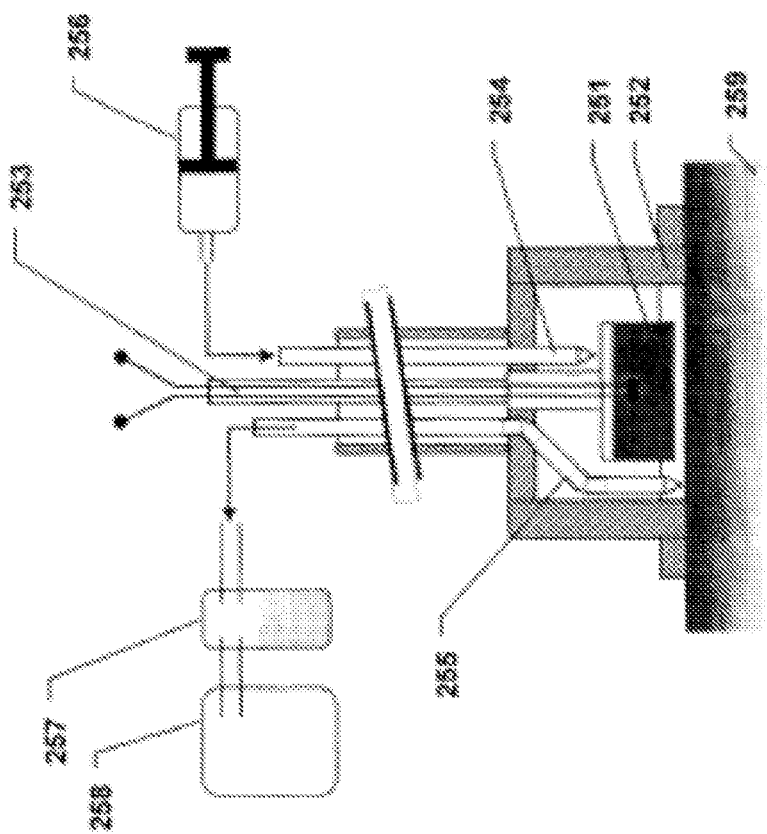
FIG. 2b illustrates an example embodiment of an apparatus for solubilizing tissue.

The term "selectively" as used throughout the specification and claims refers to a condition of a component wherein an operator of the apparatus or software configured to control the apparatus may activate or deactivate the feature or function of the component as is necessary or desired in use of the apparatus.

The term "operatively connected" as used throughout the specification and claims means that the identified components are connected in a way to perform a designated function.

In one embodiment, an apparatus for obtaining a solubilized sample from tissue is provided, the apparatus comprising: an energy source configured to be operatively connected to the tissue; a reservoir housing configured to be operatively connected to the tissue, wherein the reservoir housing is configured to apply a liquefaction promoting medium ("LPM") to the tissue.

As illustrated in FIGS. 1a-1c, in one embodiment the apparatus includes an energy source in the form of a rotary abrasive component 101 attached to a support shaft 102, which is in turn attached to a rotary motor 103. In one embodiment the apparatus includes a battery pack 104 configured to power motor 103 and cause abrasive component 101 to move. The apparatus further comprises a reservoir housing 105 configured to form the structure of the apparatus and allow for manipulation of the apparatus over a tissue of interest. In one embodiment, reservoir housing 105 includes an opening in the portion of reservoir housing 105 configured to be applied to a tissue of interest, wherein the opening is configured to allow abrasive component 101 to contact the tissue of interest. Reservoir housing 105 may contain or be configured to contain LPM. The opening in reservoir housing 105 may be temporarily sealed using an abradable sheet 106 that is configured to prevent escape of any LPM contained within reservoir housing 105 until activation of abrasive component 101, which is configured to destroy abradable sheet 106 and permit contact of LPM to a tissue of interest. In one embodiment, the apparatus is configured to be set in intimate contact with a tissue surface 107. In one embodiment, LPM is stored in a sample container 108, which is configured to selectively allow transfer of LPM into reservoir housing 105. In one embodiment, as illustrated in FIG. 1b, sample container 108 is contained within reservoir housing 105. In another embodiment, sample container 108 is outside reservoir housing 105. LPM is transferred from sample container 108 into reservoir housing 105 and is contained by abradable sheet 106 prior to activation of abrasive component 101, after which abrasive component 101 is activated and abradable sheet 106 is destroyed, allowing LPM to contact tissue surface 107. Contact of abrasive component 101 and LPM with tissue surface 107 may result in tissue solubilization. Abradable sheet 106 may include a thin sheet of paper, a rubber sheet, metal foil, a plastic sheet, any water-soluble sheet, and any other appropriate sheet of material.

In one embodiment, reservoir housing 105 is configured to collect the solubilized sample from tissue surface 107. In one embodiment, as illustrated in FIG. 1c, upon completion of the solubilization process, motor 103 stops and LPM (now containing solubilized tissue constituents) is transferred via a suction pump 109 to a sample container 110. In another embodiment, (not illustrated), upon completion of the solubilization process, motor 103 stops and LPM (now containing solubilized tissue constituents) is transferred into a pre-vacuumized container. In yet another embodiment (not illustrated), upon completion of the solubilization process, motor 103 stops and LPM (now containing solubilized tissue constituents) is transferred to sample container 110 through any means, including for example, by way of gravity.

In one embodiment, as illustrated in FIG. 1d, abrasive component 101 may be attached to a support shaft having multiple sections 1021 and 1022, which are configured to move in relation to one another. In this embodiment, the support shaft may optionally include a pressure-sensitive spring 1023 configured to sense the pressure experienced within the support shaft between sections 1021 and 1022. In another embodiment, the support shaft having multiple sections 1021 and 1022 includes a piezoelectric crystal (not illustrated) for monitoring and controlling pressure applied to the tissue by monitoring pressure within the support shaft between sections 1021 and 1022.

In another embodiment, as illustrated in FIG. 1e, the apparatus includes a sponge-bellow assembly configured to at least one of store LPM, release LPM, or collect a solubilized sample from a tissue. In one embodiment, a sponge 111 is configured in a flexible bellow-shaped housing 112, wherein sponge 111 is at least partially saturated with LPM. In this embodiment, as the apparatus is pressed against tissue surface 107, the sponge-bellow housing 112 is compressed causing sponge 111 to release LPM into the reservoir housing. Upon removal of the apparatus from tissue surface 107, the sponge-bellow housing 112 expands to its original size, causing sponge 111 to at least partially absorb LPM and tissue constituents. In another embodiment, sponge 111 is not configured to be filled with LPM, but rather is configured to absorb the solubilized sample and tissue constituents following application of energy to tissue surface 107. In one embodiment, sponge 111 is configured to be filled with LPM, and is configured to release LPM, which is later collected along with tissue constituents into sample container 110. FIGS. 1e-1g illustrate sequential steps of use of one example embodiment of the apparatus having a sponge-bellow assembly.

Figure 2A:
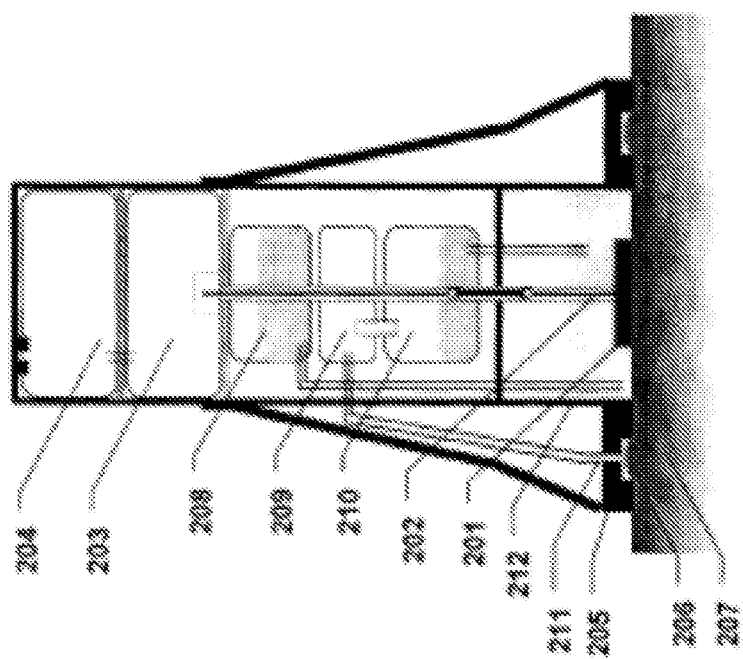
FIG. 2a illustrates an example embodiment of an apparatus for solubilizing tissue.

FIG. 2a illustrates another example embodiment of the apparatus, including an energy source in the form of a rotary abrasive component 201. Abrasive component 201 is attached to a shaft 202, which is in turn attached to a rotary motor 203. A battery pack 204 is included to power motor 203. In one embodiment, a flanged housing 205 is configured to substantially encircle the reservoir housing. Flanged housing 205 defines a chamber 206 located therein and configured to substantially encircle the reservoir housing. Flanged housing 205 and chamber 206 are configured to be operatively connected to a tissue surface 207. In one embodiment, chamber 206 is operatively connected a suction pump 209, which is configured to create an air pressure less than ambient air pressure within chamber 206, thereby facilitating a vacuum-assisted seal between tissue surface 207 and flanged housing 205, which may prevent LPM and/or the solubilized tissue sample from leaking from the reservoir housing. In one embodiment, the apparatus further comprises a cartridge 208 configured to contain and selectively distribute LPM into the reservoir housing. Suction pump 209 may be operatively connected to a sample container 210, and configured such that solubilized tissue and/or LPM is transported from the reservoir housing and into sample container 210.

In another embodiment, as illustrated in FIG. 2b, the energy source comprises a piezoelectric element 251 within the reservoir housing 252. Piezoelectric element 251 is a transducer of electrical energy, which is supplied via circuitry provided in a flexible tubing 253. The apparatus further includes a flexible tubing 254 configured to extend into reservoir housing 252, and which is configured to selectively introduce LPM into reservoir housing 252. The apparatus may further include a flexible tubing 255 configured to remove LPM and/or a solubilized tissue sample from reservoir housing 252. In one embodiment, flexible tubing 254 is operatively connected to an injection system 256, which is configured to selectively introduce LPM into reservoir housing 252. In another embodiment, flexible tubing 255 is operatively connected to a sample container 257, which in turn is operatively connected to a suction pump 258, and is thereby configured to allow transfer of LPM and/or a solubilized tissue sample from reservoir housing 252 and into sample container 257. In one embodiment, suction pump 258 is further configured to create a vacuum-assisted seal between the apparatus and a tissue surface 259. In another embodiment, suction pump 258 is configured to provide an additional energy source for solubilization. In one embodiment, the apparatus is configured to be moved over an area of tissue surface 259, thereby permitting the collection of samples from various tissues. In this embodiment, LPM may be continuously provided to reservoir housing 252 by flexible tubing 254, while samples are continuously transported to sample container 257 by flexible tubing 255.

With continued reference to FIG. 2b, in another embodiment, piezoelectric element 251 may be eliminated, and tissue solubilization may be achieved by any energy source. In another embodiment, the energy source is pressure supplied by injection system 256. In yet another embodiment, the energy source is a vacuum supplied by suction pump 258.

Figure 2C:
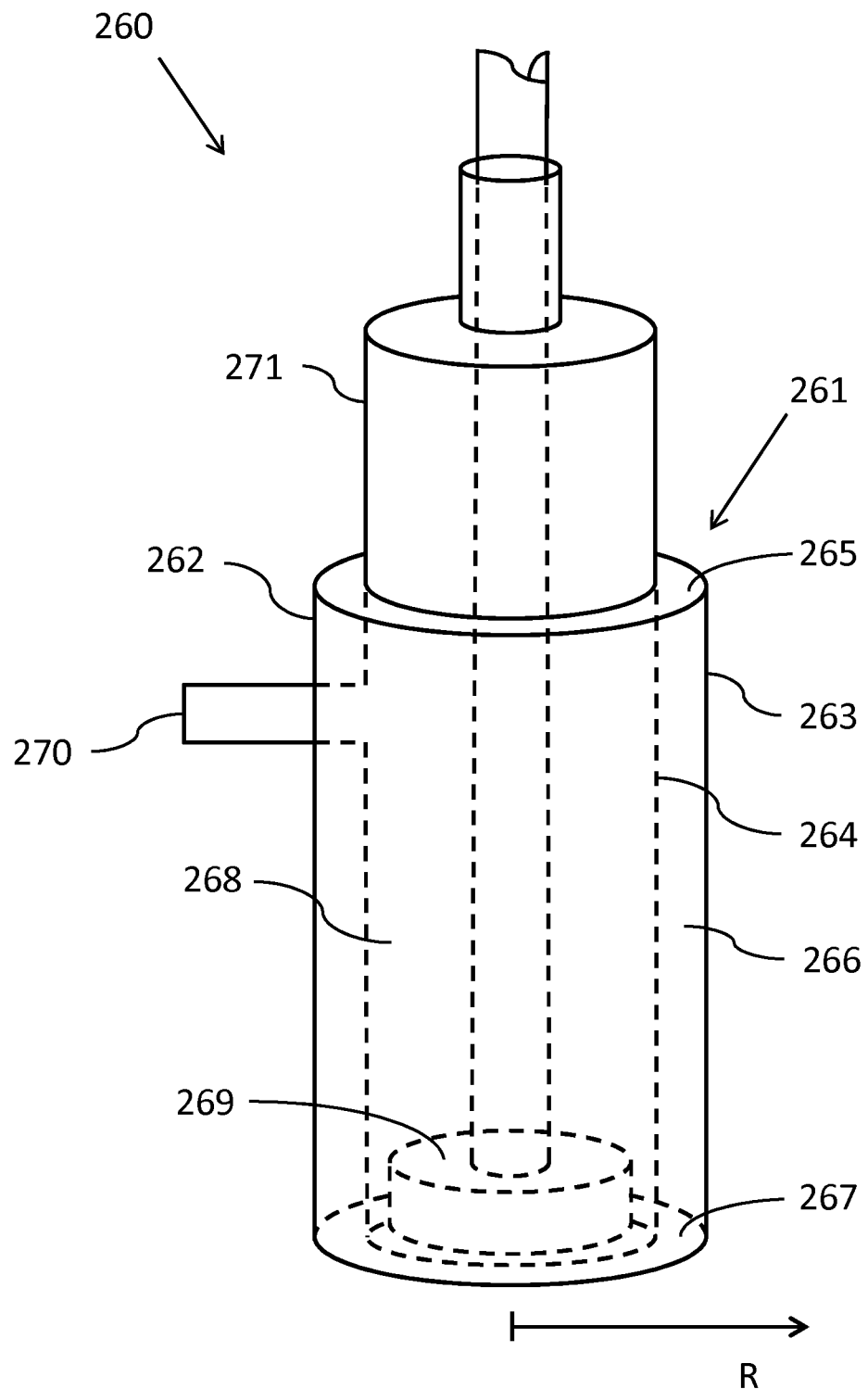
FIG. 2c illustrates an example embodiment of an apparatus for solubilizing tissue.

In one embodiment, as illustrated in FIG. 2c, an apparatus 260 for solubilizing tissue includes a housing 261. In one embodiment, housing 261 further includes a vacuum chamber 262. The vacuum chamber includes an outer wall 263, an inner wall 264, and an upper wall 265. The vacuum chamber additionally includes an interior 266, which is defined by outer wall 263, inner wall 264, and upper wall 265. In one embodiment, inner wall 264 is radially inward of outer wall 263, wherein R defines a radially outward direction. The vacuum chamber may additionally include an open end 267 configured to contact a tissue surface. In another embodiment, interior 266 is configured to be operatively connected to a tissue surface. In one embodiment, housing 261 additionally includes a passage 268, which is configured to be operatively connected to a tissue surface. In one embodiment, vacuum chamber 262 is configured to selectively generate an air pressure within interior 266 that is less than the pressure of ambient air surrounding the apparatus. In one embodiment, vacuum chamber 262 is configured to create a vacuum-assisted seal between the apparatus and a tissue surface. In another embodiment, passage 268 is configured to selectively contain LPM and vacuum chamber 262 is configured to remove LPM that is applied to the tissue surface within passage 268. In another embodiment, apparatus 260 additionally includes an energy source 269 that is configured to be operatively connected to the tissue surface through passage 268. Energy source 269 may be any energy source as described within this specification. In one embodiment, energy source 269 is a mechanical energy source having an abrasive disc attached to a shaft extending through passage 268. In one embodiment, apparatus 260 includes a port 270 configured to extend into passage 268 and configured to selectively allow introduction of LPM into the passage. In another embodiment, port 270 is configured to extend into passage 268 and configured to selectively allow removal of a solubilized tissue sample from passage 268. In another embodiment, apparatus 260 includes a sample container 271. In still another embodiment, at least a portion of sample container 271 is positioned within at least a portion of passage 268.

With continued reference to FIG. 2c, in one embodiment, vacuum chamber 262 is operatively connected to a suction device (not shown), which is capable of creating a vacuum within vacuum chamber 262. In another embodiment, suction device (not shown) is capable of creating an air pressure within the vacuum chamber interior 266 that is less than ambient air pressure. In one embodiment, at least outer wall 263 is configured to be flexible and biased toward a radially outward direction as defined by R. At least a portion of outer wall 263 may be configured to be displaced radially inwardly, and released, resulting in the generation of an air pressure within vacuum chamber interior 266 that is less than ambient air pressure.

In one embodiment, apparatus 260 includes a port (not shown) operatively connected to sample container 271 and configured to at least one of: selectively allow introduction of LPM into vacuum chamber 262, and selectively allow removal of a solubilized sample from vacuum chamber 262. In one embodiment, sample container 271 is configured to contain LPM prior to application to the tissue. In another embodiment, sample container 271 is configured to contain a solubilized tissue sample following solubilization of the tissue. In another embodiment, LPM is contained in a reservoir prior to application to the tissue. In one embodiment, the reservoir is sample container 271.

Figure 2D:
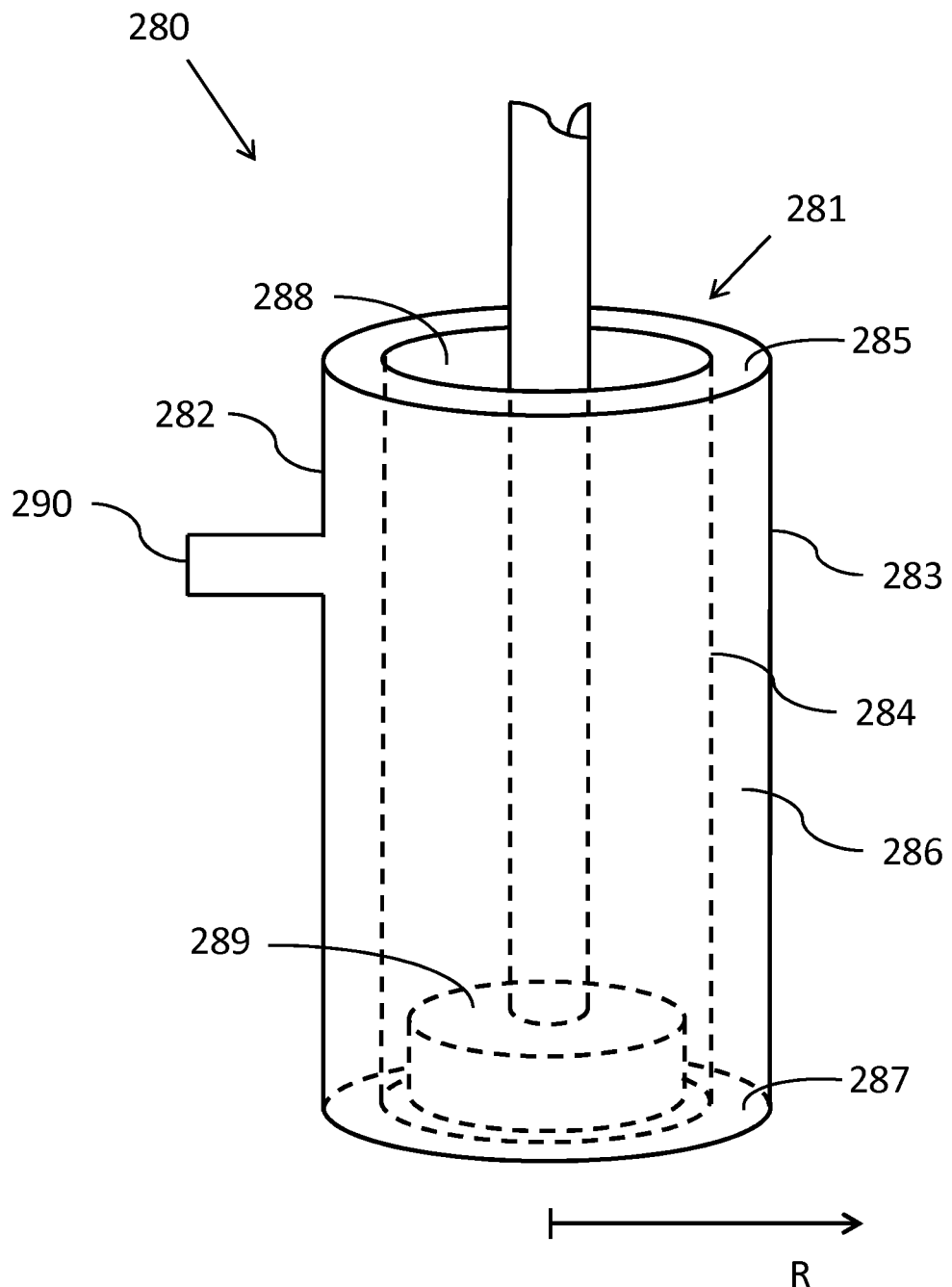
FIG. 2d illustrates an example embodiment of an apparatus for solubilizing tissue.

In another embodiment, as illustrated in FIG. 2d, an apparatus 280 for solubilizing tissue includes a housing 281 and a vacuum chamber 282. In one embodiment, vacuum chamber 282 includes an outer wall 283, an inner wall 284, an upper wall 285, and an interior 286 defined by outer wall 283, inner wall 284, and upper wall 285. In another embodiment, vacuum chamber 282 includes an open end 287 configured to contact a tissue surface. In one embodiment, interior 286 is configured to be operatively connected to a tissue surface. In one embodiment, apparatus 280 includes a passage 288, through which an energy source 289 is operably connected to the tissue. In one embodiment, passage 288 is configured to be operatively connected to a tissue surface. Energy source 289 may be any energy source described herein. In one embodiment, apparatus 280 includes a port 290 operatively connected to vacuum chamber 282. Port 290 is configured to selectively allow introduction of LPM into vacuum chamber 282, and/or selectively allow removal of a solubilized tissue sample from vacuum chamber 282. In one embodiment, a sample container (not shown) is configured to receive a solubilized tissue sample from apparatus 280 via port 290. In one embodiment, vacuum chamber 282 is configured through open end 287 to provide a vacuum-assisted seal to a tissue surface. In another embodiment, inner wall 284 is configured to permit selective transport of a LPM into passage 288, or removal of a solubilized sample from passage 288. Inner wall 284 may facilitate transport of LPM or solubilized sample to and from passage 288 by any of the following: a port within inner wall 284 (not shown), perforations within inner wall 284 (not shown), or a porous structure within inner wall 284 configured to permit selective or limited transfer of a liquid. In one embodiment, inner wall 284 does not extend all the way to a tissue surface, while outer wall 283 does extend to a tissue surface.

In some embodiments, the LPM is a composition configured to at least one of disaggregate, solubilize, liquefy, stabilize, remodel, or remove a tissue of interest, or components thereof. In other embodiments, the LPM is a composition configured to dislodge tissue constituents. In another embodiment, the LPM is configured to identify at least one analyte from the tissue. In one embodiment, the LPM is any fluid medium that when combined with an energy source, is capable of solubilizing a tissue of interest. Suitable LPM compositions are disclosed in U.S. patent application Ser. Nos. 12/664,994 and 13/126,105, each of which is incorporated by reference herein in their entireties.

In one specific embodiment, a suitable LPM composition comprises 3-(decyl dimethyl ammonio) propane sulfonate and polyethylene glycol dodecyl ether. In one embodiment, the polyethylene glycol dodecyl ether comprises tetraethylene glycol dodecyl ether. In one embodiment, the 3-(decyl dimethyl ammonio) propane sulfonate and the polyethylene glycol dodecyl ether are present in a total concentration of from about 0.01% (w/v) to about 5% (w/v) in a buffer solution. In one embodiment, the 3-(decyl dimethyl ammonio) propane sulfonate and the polyethylene glycol dodecyl ether are present in a total concentration of about 0.5% (w/v) in a buffer solution. In one embodiment, the 3-(decyl dimethyl ammonio) propane sulfonate and the polyethylene glycol dodecyl ether are present in ratio of from about 3:2 to about 2:3.

Energy Source

In one embodiment, the energy source is configured to be operatively connected to the tissue, including, in one embodiment, in direct contact with the tissue. In one embodiment, the energy source is configured to apply energy to the tissue. In another embodiment, the energy source is configured to apply energy to the tissue within the reservoir housing. In one embodiment, the reservoir housing comprises at least a portion of the energy source. In another embodiment, the energy source is configured to apply energy to the tissue outside the reservoir housing.

In one embodiment, the energy source is configured to apply energy to the tissue within a reservoir housing, while the energy source may be located within or outside the reservoir housing. In one embodiment, the reservoir housing is configured to be placed in contact with the tissue and expose the tissue to the energy source, thereby allowing energy to be applied to the tissue with minimal interference. In another embodiment, the reservoir housing contains LPM and is optionally configured to allow contact of the LPM with the tissue upon application of energy.

In one embodiment, a diagnostic device and an energy source are operatively connected to the reservoir housing. The energy source may include electrical circuitry configured to measure tissue resistance and analyte concentration measurements, and display thereof. The energy source and diagnostic device may be operatively connected to the tissue of interest, upon which the energy source applies energy to the tissue, either alone or in combination with other physical, mechanical, electrical, or chemical forces.

In one embodiment, the energy source is configured to apply at least one of the following forms of energy to the tissue: ultrasound energy, mechanical energy, optical energy, thermal energy, and electrical energy. In another embodiment, the energy source is configured to apply energy to the tissue in a form that is not a heated liquid.

In one embodiment, the energy source applies ultrasound energy to the tissue of interest. Any variety of ultrasound devices may be used or readily adapted for use in tissue solubilization. Generally speaking, any ultrasound device configured to be applied to tissue to solubilize the tissue, solubilize analytes of interest, and collect such analytes, is suitable for use in tissue solubilization.

In one embodiment, an ultrasound device utilizing focused or channeled ultrasound is used. In another embodiment, the ultrasound device includes an ultrasound transducer and channeling means connected to an electrical signal generator and amplifier, which provides the driving and controlling mechanism for the transducer. In another embodiment, the device includes a vacuum pump and current generator.

In one embodiment, the ultrasound device includes an ultrasound delivery chamber having an ultrasound transducer connected to an electrical signal generator and amplifier through electrical contacts. In one embodiment, the ultrasound device is located within the reservoir housing. In another embodiment, the ultrasound device is located outside the reservoir housing. The ultrasound transducer may be opposite the surface of the ultrasound delivery chamber that is contacted to the tissue. The ultrasound delivery chamber may be made from one or more of a polymer, a metal, and any other appropriate material, while the interior walls of the chamber are optimally made from a material that reflects acoustic energy. The interior walls of the ultrasonic delivery chamber may be made of a polymer, a metal, and any other appropriate material. In one embodiment, the ultrasonic delivery chamber includes interior walls that form one or more of the following shapes: a truncated cone oriented such that the large opening is adjacent to the transducer while the small opening is adjacent to the tissue; a horn oriented such that the large opening is adjacent to the transducer and the small opening is adjacent to the tissue; and a hemisphere oriented such that the rounded portion is adjacent to the transducer.

In one embodiment, the ultrasonic delivery chamber is filled at least partially with LPM. In another embodiment, the ultrasonic delivery chamber is directly contacted to the tissue, and includes an adhesive layer on its tissue-contacting surface to attach the chamber to the tissue.

In one embodiment, the ultrasonic delivery chamber is operatively connected to a vacuum pump though a port that opens into the LPM. In another embodiment, the ultrasonic delivery chamber includes additional means for applying force to the tissue. In one embodiment, a pair of electrodes is operatively connected to the tissue to apply electric current thereto, which may result in enhanced solubilization of the tissue. In yet another embodiment, the ultrasonic delivery chamber includes one or more diagnostic devices for qualitative or quantitative analysis of sampled analytes.

In one embodiment, the ultrasound transducer is utilized to control the parameters of the ultrasound energy applied through the ultrasound device. The ultrasound transducer may be one or more of a piezo, ceramic, or polymer block, or any other device. In one embodiment, the ultrasound transducer is operated at an appropriate frequency as determined by the operator of the apparatus, or software. In another embodiment, the ultrasound transducer is operated between about 20 kHz and about 20 MHz. In yet another embodiment, the ultrasound transducer is operated between about 20 kHz and about 1 MHz. Other ultrasound parameters may be varied to achieve the desired solubilization of the tissue of interest and solubilization of the analytes of interest, including, without limitation, intensity, amplitude, duty cycle, fluence, mechanical index, thermal index, distance from the tissue, and duration.

In one embodiment, the energy source is configured to apply mechanical energy to the tissue, and the mechanical energy is applied by at least one of: a piezoelectric element, an abrasive component, a vacuum, a pressure, and a shear force. In one embodiment, the abrasive component is at least one of: a sheet of abrasive material, an abrasive disc, an abrasive ring, and a brush having bristles. In another embodiment, the abrasive component is connected to a shaft.

In one embodiment, the abrasive component is an abrasive disc, which is configured to have an abrasive surface and is made of at least one of the following: fabric, polymer, abrasive crystals, and a disc of any material bearing sand paper. In one embodiment, abrasive crystals include at least one of the following: quartz, metal, silica, silicon carbide, dust and derivatives of aluminum (such as $AlO_2$), and diamond dust.

In one embodiment, the abrasive component includes sand paper, which may be coated with abrasive crystals. In another embodiment, the abrasive component utilizes sand paper having a grit size between about 40 and 2,000. In another embodiment, the abrasive component utilizes sand paper having any appropriate grit size.

Figure 3A:
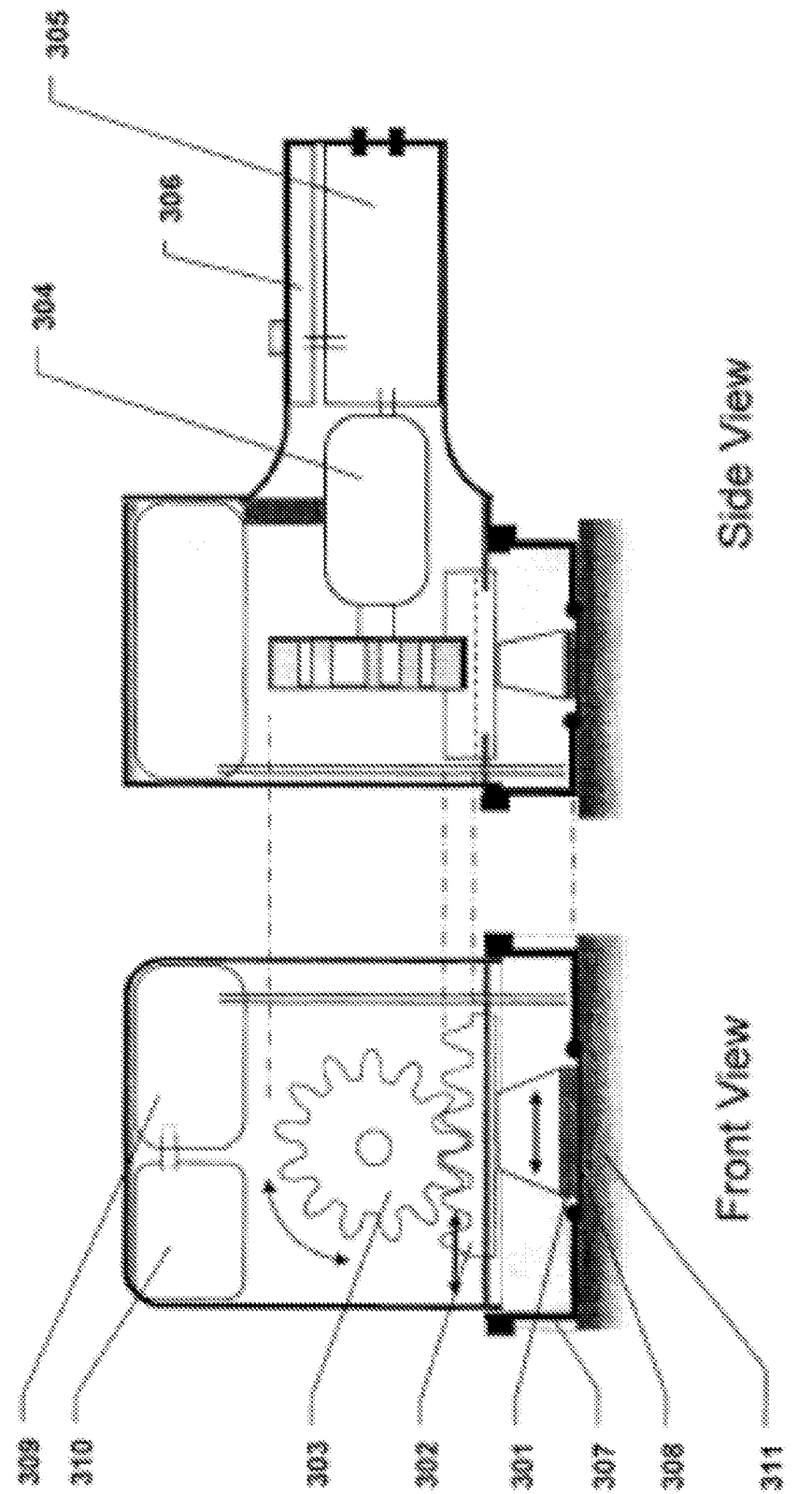
FIG. 3a illustrates front and side views of an example embodiment of an apparatus for solubilizing tissue.

In another embodiment, illustrated in FIG. 3a, the energy source is an oscillating abrasive component 301, which is attached to a rack 302 and pinion 303. Pinion 303 may be operatively connected to a motor 304. In one embodiment, motor 304 is power by a battery pack 305, and controlled by a microchip controller 306. In another embodiment (not illustrated), movement of abrasive component 301 is achieved through some other means; for example, abrasive component 301 may be connected to a linear motor, linear motion actuators, a ball screw assembly, a leadscrew assembly, a jackscrew assembly, or any other device configured to translate rotational motion to linear motion. In one embodiment, abrasive component 301 is configured to oscillate within reservoir housing 307. Reservoir housing 307 may include an opening adjacent to oscillating abrasive component 301, which is temporarily sealed by a abradable sheet 308. In one embodiment, LPM is stored within reservoir housing 307 and sealed by abradable sheet 308. In another embodiment, LPM may be selectively transferred to reservoir housing from a storage container located elsewhere. In one embodiment, the apparatus includes a sample container 309, which is configured to be operatively connected to a suction pump 310. Upon activation of abrasive component 301, abradable sheet 308 is destroyed allowing LPM to contact a tissue surface 311. Suction pump 310 is then selectively activated to transport LPM and/or a solubilized tissue sample into sample container 309. In one embodiment, any of the components, or the apparatus itself, is designed to be disposable.

Figure 3C:
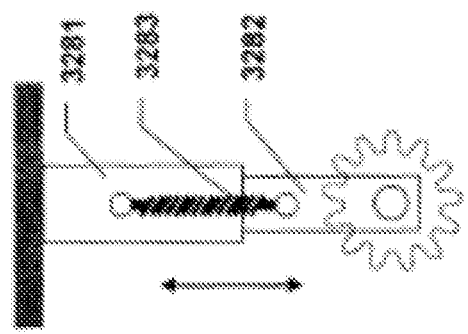
FIG. 3c illustrates an example embodiment of a support shaft component of an energy source for use in an apparatus for solubilizing tissue.
Figure 3B:
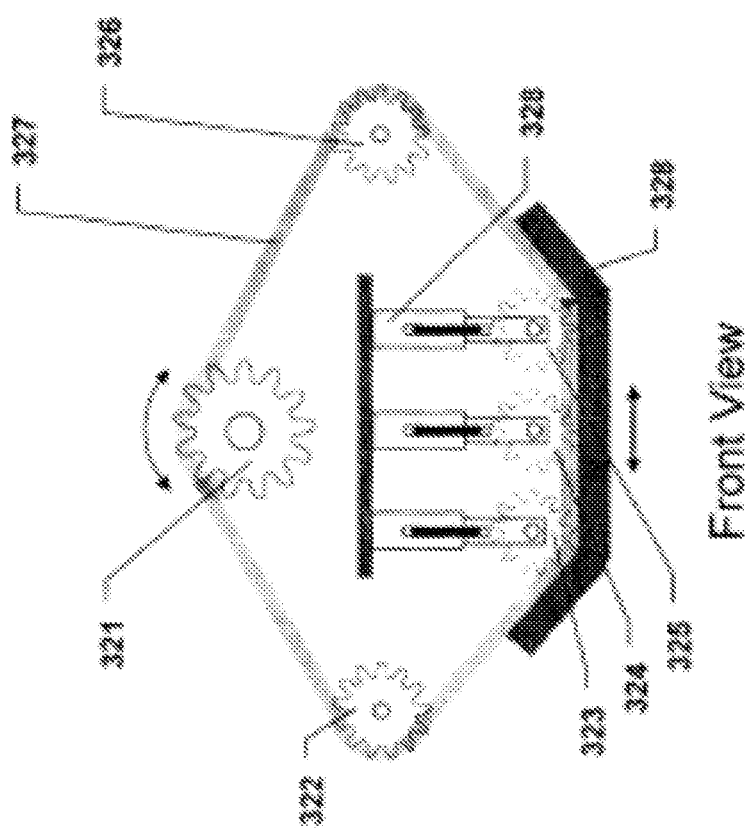
FIG. 3b illustrates front and side views of an example embodiment of an apparatus for solubilizing tissue.

In another embodiment, as illustrated by FIG. 3b, the energy source is a series of gears 321, 322, 323, 324, 325, and 326 about which a belt 327 is mounted. Belt 327 is operably connected to an abrasive component 328, which is configured to move in a linear oscillatory motion when gear 321 is driven by motor 304 in an oscillatory rotation motion. In one embodiment, at least one shaft is configured to be fixed to the reservoir housing and is operably connected to one or more of gears 323, 324, and 325. In this embodiment, abrasive component 328 is permitted to contour with a non-flat tissue surface. Additionally, the at least one shaft may be configured to sense and control the pressure applied by abrasive component 328 to a tissue surface. As illustrated in FIG. 3c, the at least one shaft may comprise two independent sections 3281 and 3282, which move independently of one another and are connected by a pressure sensitive spring 3283.

Figure 4F:
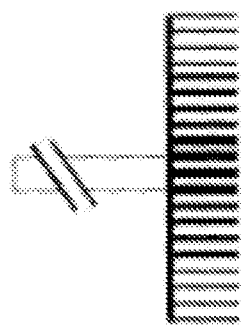
FIG. 4f illustrates an example embodiment of an abrasive component of an energy source for use in an apparatus for solubilizing tissue.
Figure 4E:
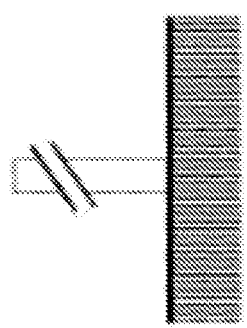
FIG. 4e illustrates an example embodiment of an abrasive component of an energy source for use in an apparatus for solubilizing tissue.
Figure 4G:
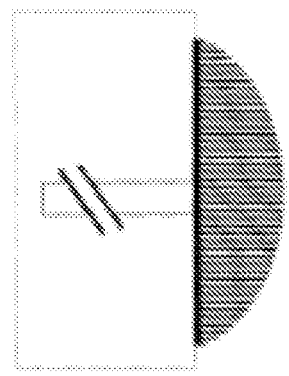
FIG. 4g illustrates an example embodiment of an abrasive component of an energy source for use in an apparatus for solubilizing tissue.
Figure 4B:
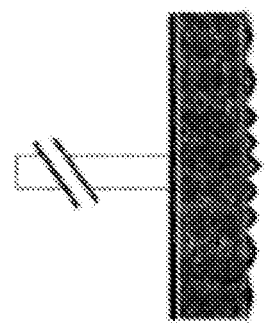
FIG. 4b illustrates an example embodiment of an abrasive component of an energy source for use in an apparatus for solubilizing tissue.
Figure 4D:
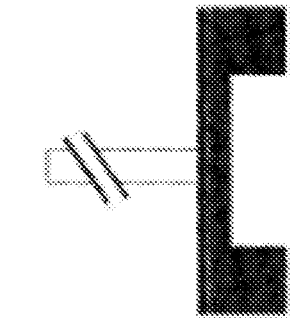
FIG. 4d illustrates an example embodiment of an abrasive component of an energy source for use in an apparatus for solubilizing tissue.
Figure 4A:
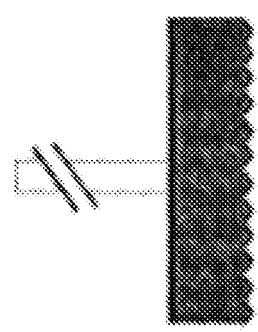
FIG. 4a illustrates an example embodiment of an abrasive component of an energy source for use in an apparatus for solubilizing tissue.
Figure 4C:
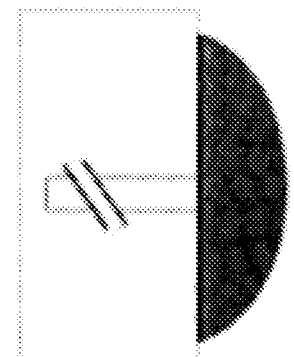
FIG. 4c illustrates an example embodiment of an abrasive component of an energy source for use in an apparatus for solubilizing tissue.

In another embodiment, as illustrated by FIG. 4a, the energy source is an abrasive component comprising a sheet of abrasive material having a substantially uniform thickness. Abrasive materials may include, without limitation, a fabric, abrasive crystals (e.g., quartz, metal, silica, silicon carbide, dust, and derivatives of aluminum (such as $AlO_2$)), diamond dust, polymeric and natural sponge, and any other abrasive material. In one embodiment, the abrasive component is configured to have a heterogeneous abrasiveness—for example, the component can have spatial variation of abrasiveness. In another embodiment, illustrated in FIG. 4b, the abrasive component is a disc configured to have a gradient of abrasiveness—for example, high abrasiveness at the center of the disc, and low abrasiveness at the disc periphery. In another embodiment, as illustrated in FIG. 4c, the abrasive component can have a non-planar contact face—for example, a rounded cross-section. In one embodiment, the rounded surface has an aspect ratio (ratio of height to width) that varies from 10.0 to 0.1. In yet another embodiment, as illustrated by FIG. 4d, the abrasive component may have a tissue contact face that is substantially ring-shaped.

In one embodiment, the abrasive component includes a brush having bristles, and which bristles have a stiffness measured by the Robertson number ranging between about 1 and about 15. In another embodiment, the brush utilizes bristles having varied stiffness. In one embodiment, the length of the bristles is between about 0.5 mm and about 20 mm. Bristles of lesser or greater lengths may additionally be used. In one embodiment, the brush is configured such that the bristles form a contact angle with the tissue that is between about 0 degrees and about 90 degrees. The bristles may be made of natural or synthetic material, or combinations thereof, and can include animal fibers, metal, and polymers. The bristles may have a cross-sectional shape configured to achieve certain desired level of abrasion of the tissue of interest. Such cross-sectional shapes may include, without limitation, round, square, triangular, and polygonal.

In another embodiment, as illustrated by FIG. 4e, the abrasive component is a brush having bristles of uniform height and abrasiveness. In another embodiment, as illustrated in FIG. 4f, the abrasive component is a brush having bristles of different lengths and/or abrasiveness. In still another embodiment, as illustrated in FIG. 4g, the abrasive component is a brush having bristles of different lengths forming a smooth and rounded tissue contact face, wherein the rounded surface has an aspect ratio that varies from 10.0 to 0.1.

It is understood that in any configuration, the abrasive component may be configured such that its abrasive surface, or abrasive surfaces, are contacted to the tissue of interest. In one embodiment, the contact area of the abrasive surface is up to about 10 $cm^2$. In another embodiment, the contact area of the abrasive surface is greater than about 10 $cm^2$. In one embodiment, the contact area is selectively chosen depending upon the quantity of analytes to be sampled and/or the area of the tissue to be inspected.

In one embodiment, the abrasive component is applied to the tissue of interest with a selectively chosen pressure. In another embodiment, the abrasive component is applied to the tissue of interest with a pressure of up to about 2,000 $N/m^2$. In yet another embodiment, the abrasive component is applied to the tissue of interest using a pressure of between about 1 $N/m^2$ and about 2,000 $N/m^2$. In another embodiment, the abrasive component is applied to the tissue of interest using a pressure of between about 100 $N/m^2$ and about 1,000 $N/m^2$. In still another embodiment, the abrasive component is applied to the tissue of interest using a pressure greater than 2,000 $N/m^2$. The pressure at which the abrasive component is applied to the tissue may be carefully controlled to prevent undesirable over-abrasion of the tissue of interest.

In one embodiment, the abrasive component is contacted directly to the tissue of interest for a duration ranging from about 1 second to about 60 minutes. In another embodiment, the abrasive component is contacted to the tissue for a duration greater than about 60 minutes. Appropriate duration of contact between the abrasive component and the tissue may be selectively determined, and/or adjusted, depending upon such factors as: the tissue type, the amount of tissue constituent to be collected, and the area of tissue to be sampled.

In one embodiment, mechanical energy is applied by abrasive components in motion, which are configured to be directly contacted to the tissue of interest. In one embodiment, the abrasive component is contacted to the tissue of interest within the reservoir housing. In another embodiment, the abrasive component is contacted to the tissue of interest outside the reservoir housing. In one embodiment, the abrasive component is contacted to the tissue of interest in the presence of a LPM. The abrasive component may be configured to apply energy to the tissue of interest within the reservoir housing, which further contains LPM. Upon contacting the reservoir housing to the tissue, the abrasive component is set in motion (e.g., rotational, random orbital, translational, and/or oscillatory movement) resulting in the dislodging of tissue constituents. In one embodiment, dislodged tissue constituents are collected into the LPM.

In one embodiment, the energy source comprises an absorbent abrasive component. Absorbent abrasive devices may comprise an abrasive surface made of hard materials that can apply abrasive forces to a tissue of interest and retain the dislodged tissue constituents. In one embodiment, the abrasive surface of the absorbent abrasive device is at least one of: silica, diamond, metals, or any other hard surface. In one embodiment, the device includes an absorbent pad. The absorbent pad may be a biocompatible material that holds LPM and/or collects and holds a solubilized tissue sample. The absorbent pad may be made of an absorbent fabric with interwoven and/or embedded abrasive entities. In one embodiment, the LPM can be separated from the absorbent pad to capture the solubilized tissue sample therein that can be analytically processed for the presence or absence of one or more tissue analytes of interest.

In another embodiment, mechanical energy is applied to the tissue using abrasive forces created by a mechanized liquid stirrer. In one embodiment, the reservoir housing is configured to contain a LPM containing abrasive particles, wherein the LPM is allowed to contact the tissue, and the tissue is abraded by stirring the LPM. In one embodiment, the mechanized liquid stirrer is configured to stir the LPM at a rotation rate of up to about 50,000 rpm. In another embodiment, the mechanized liquid stirrer is configured to stir the LPM at a rotation rate greater than about 50,000 rpm, depending upon the tissue type and/or amount of tissue constituents that need to be sampled.

In another embodiment, mechanical energy is applied to the tissue using abrasive forces created by a high velocity jet of fluid. In one embodiment, the high velocity jet comprises a stream of fluid configured to move at a high velocity, wherein the fluid contains abrasive particles. In another embodiment, the abrasive particles are one or more of: silica, silicon carbide, $AlO_2$, quartz, metal, dust, diamond dust, and any other appropriate abrasive particle. The high velocity jet may be configured to apply the high velocity stream of fluid, which contains abrasive particles, at the tissue of interest resulting in the abrading of the tissue and dislodging of tissue constituents. Abraded tissue can be collected in LPM to generate a solubilized tissue sample, which can be appropriately analyzed. In another embodiment, the stream of fluid used by the high velocity jet is at least partially comprised of a LPM. In yet another embodiment, the stream of fluid is a gas.

The high velocity jet of fluid may employ a pressurized fluid generator. In one embodiment, the pressurized fluid generator is a compressor. In another embodiment, the pressurized fluid generator generates a compressed gaseous jet of air and a non-reactive gas, which carries abrasive particles. In another embodiment, the high velocity jet of fluid is configured to be selectively directed at the tissue of interest, or specific portions of the tissue of interest. In one embodiment, the jet is configured to be redirected to a sample container for collecting the dislodged tissue constituents from the jet. In one embodiment, the high velocity jet is applied to the tissue of interest such that the jet stream's contact angle with the tissue is between about 0 degrees and 90 degrees. The jet's contact angle may be selected to facilitate the jet's redirection into the sample container. In one embodiment, the sample container contains the LPM for collecting and solubilizing the abraded tissue components from the jet. In another embodiment, the device may be used in conjunction with a suction device configured to remove abraded and dislodged tissue components from the jet stream and transport them to the sample container.

In one embodiment, energy is applied to the tissue from the energy source at an intensity and a duration as selected by an operator of the apparatus or by software configured to identify an appropriate intensity and duration of energy application to the tissue. In another embodiment, intensity and/or duration of the energy applied to the tissue from the energy source is appropriately selected and/or adjusted based upon the particular tissue of interest and the particular application of the energy. In another embodiment, the intensity and/or duration of energy applied to the tissue from the energy source is appropriately selected and/or adjusted based upon the particular LPM used in the apparatus. In one embodiment, energy is applied to the tissue from the energy source for a duration that is: less than 60 seconds, greater than 60 seconds, greater than 90 seconds, or greater than 120 seconds. Alternate durations are optimal and appropriate in some situations. In one embodiment, the energy is applied to the tissue by the energy source at an intensity as is appropriate to solubilize and capture an analyte of interest.

In one embodiment, the energy source is configured to apply energy to the tissue at least one of before, during, or after exposure of LPM to the tissue. In another embodiment, the energy source is configured to apply energy to the tissue during the entire duration of exposure of LPM to the tissue. In yet another embodiment, the energy source is configured to selectively apply energy to the tissue in relation to the exposure of LPM to the tissue, as is deemed appropriate by an operator of the apparatus, or by software configured to identify a duration of energy application to the tissue.

Use of high energy is limited by its adverse effect on the tissue or tissue constituents. In one embodiment, a temperature sensing element (e.g., a thermocouple) is incorporated into the energy source. The temperature sensing element may be configured to monitor temperature of at least one of the energy source, LPM, and tissue. The temperature sensing element may be configured to alert an operator and/or software of an adversely high temperature in at least one of the energy source, LPM, and tissue. In one embodiment, the temperature sensing element may be configured to limit the energy source upon identification of an adversely high temperature in at least one of the energy source, LPM, and tissue.

In another embodiment, as illustrated in FIGS. 5a-5d, an apparatus is additionally configured to measure a tissue's electrical conductivity. While high energy exposure favorably solubilizes tissues, its use may lead to significant adverse effects such as injurious tissue damage. Accordingly, it may be necessary to incorporate certain components into the apparatus that provide temporal monitoring (ideally, in real-time) of the change in tissue properties—for example, tissue's electrical conductivity. In one embodiment, temporal monitoring and measurement of tissue's electrical conductivity during the solubilization process is performed by applying a predefined AC electrical voltage across a tissue using a measurement electrode 501 and a reference electrode 502. In one embodiment, measurement electrode 501 is placed directly on the tissue surface 503, while reference electrode 502 is placed in the vicinity of the region on tissue surface 503 that is being solubilized. An electrical current across measurement electrode 501 and reference electrode 502 is measured by an ammeter 504. In one embodiment, measurement electrode 501 is electrically connected to LPM, or directly connected to region of tissue surface 503 being solubilized. In one embodiment, electrical current is transmitted to an isolated stud 505 by a sliding electrical contact 506, which is fastened to a support shaft 510 immersed in LPM. In another embodiment, the reference electrode is instead a handheld cylindrical electrode 507 that is electrically connected with the electrical conductivity measurement components contained in the apparatus. In another embodiment, the reference electrode is a patch electrode 508 that is electrically connected with the electrical conductivity measurement components contained in the apparatus. In another embodiment, measurement electrode 501 is located as an inner surface lining of the reservoir housing 509.

In one embodiment, the energy source is configured to apply a mechanical energy to the tissue, and the mechanical energy is applied by a microneedle-based device having a plurality of microneedles. In one embodiment, the microneedle-based device includes a patch of microneedles. The patch of microneedles may be mechanically inserted into the tissue. In another embodiment, the patch of microneedles is configured to inject a fluid, such as LPM, into the tissue through the microneedles.

In another embodiment, as illustrated in FIGS. 6a-6e, the energy source may include a microneedle-based component. Microneedle-based devices apply energy to tissues through mechanical disruption of tissue components which is primarily accomplished by pressing microneedles into the tissue. FIG. 6a illustrates one embodiment of a microneedle patch 601 including a plurality of microneedles 602. In one embodiment, the microneedles are pre-filled with LPM. Microneedles 602 can be inserted into the tissue of interest allowing disruption and dissolution of tissue components. In another embodiment, the LPM is aspirated from patch 601 for analysis following solubilization of the tissue of interest.

In another embodiment, as illustrated in FIG. 6b, additional energy is applied to the tissue following the insertion of microneedles into the tissue. In one embodiment, microneedle patch 601 is operatively connected to a vibratory component 603, which is activated after insertion of microneedles 602 into the tissue of interest. In one embodiment, vibratory component 603 is activated following insertion of microneedles 602 into the tissue, such that vibratory component 603 vigorously shakes microneedles 602 inside the tissue. In one embodiment, the microneedle-based component is operatively connected to the reservoir housing 604. In another embodiment, reservoir housing 604 additionally contains a compressed air container 605 and a suction pump 606. Compressed air container 605 can be configured to force LPM through patch 601 and microneedles 602 into the tissue. Suction pump 606 can be configured to apply a vacuum for withdrawing LPM from the tissue. In one embodiment, compressed air container 605 and suction pump 606 may be repeatedly and alternately activated to repeatedly inject and withdraw LPM from the tissue for enhanced solubilization. In one embodiment, a battery operated electronic circuit board 607 may be included to power and control compressed air container 605 and/or suction pump 606. In one embodiment, suction pump 606 is operatively connected to a sample container to aspirate and transfer a solubilized tissue sample from patch 601 to the container. In another embodiment, as illustrated in FIG. 6d, a flexible cap 608 may be fitted to the top of patch 601. Flexible cap 604 may be biased toward a position away from patch 601 and may be repeatedly pressed inwardly toward patch 601 and allowed to retract upwardly such that LPM is repeatedly injected and withdrawn from the tissue through microneedles 602.

In another embodiment, as illustrated in FIG. 6c, vibratory component 603 includes a plurality of mechanical vibrators 6031 and a battery-operated electronic circuit board 6032 for powering and controlling the motion and direction of mechanical vibrators 6031. In one embodiment, mechanical vibrators 6031 can be vibrated in directions parallel and perpendicular to the axis of microneedles 602.

In another embodiment, as illustrated in FIG. 6e, microneedles 602 are coated with a substance 610 to enhance tissue solubilization. In one embodiment, substance 610 is an abrasive material which enhances disruption of tissue constituents for faster dissolution in LPM. In another embodiment, substance 610 is an enzyme that may cleave specific tissue components such as extracellular matrix for enhanced tissue solubilization. In yet another embodiment, substance 610 is a molecule that specifically binds to tissue analytes of interest resulting in enhanced recovery of the analyte from the tissue. In still another embodiment, substance 610 is an antibody.

Figure 6F:
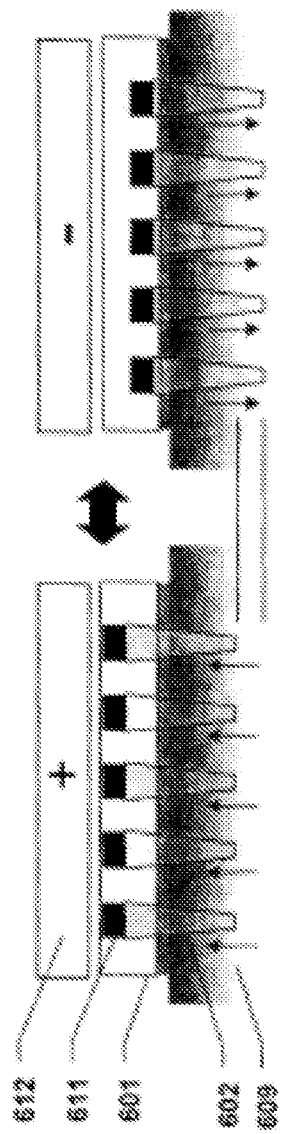
FIG. 6f illustrates an example embodiment of a microneedle-based component of an energy source for use in an apparatus for solubilizing tissue.
Figure 6G:
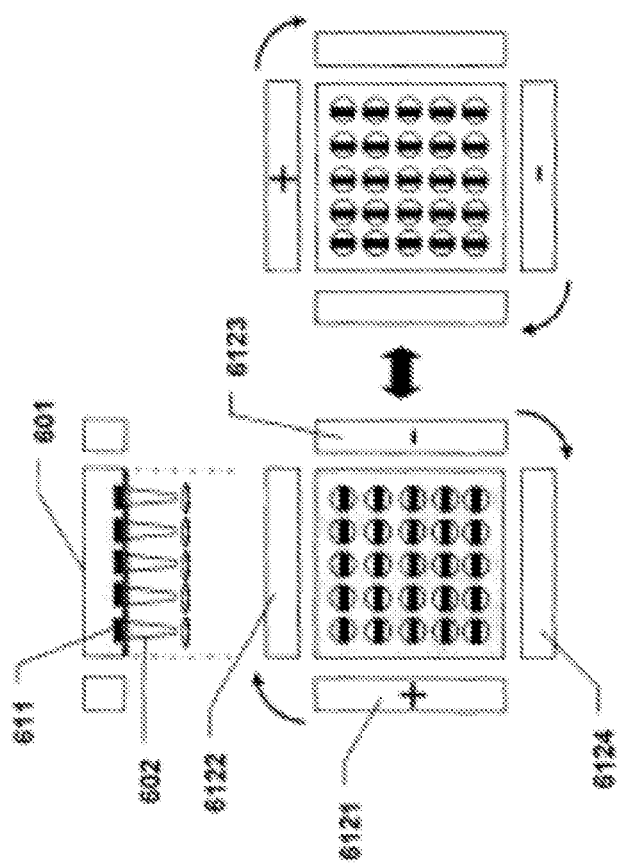
FIG. 6g illustrates an example embodiment of a microneedle-based component of an energy source for use in an apparatus for solubilizing tissue.

In another embodiment, as illustrated in FIG. 6f, motion of microneedles 602 after insertion into the tissue is produced through use of an electromagnet 612. In one embodiment, electromagnet 612 is operatively connected to patch 601 and configured to produce oscillatory motion of each microneedle 602 along its longitudinal axis. In one embodiment, such motion is achieved by fastening a magnet 611 to the top of each microneedle 602, such that magnet 611 responds to an alternating polarity profile of electromagnet 612 leading to oscillatory linear motion of microneedles 602. In another embodiment, as illustrated in FIG. 6g, rotary motion of microneedles 602 is achieved using electromagnets 6121, 6122, 6123, and 6124 placed symmetrically around patch 601. Magnet 611 attached to the top of each microneedle 602 responds to the alternating polarity profile of electromagnet 6121, 6122, 6123, and 6124 leading to rotary motion of microneedles 602.

In yet another embodiment, one or more device components illustrated in FIGS. 6a-6g are disposable and easily replaced for sterile usage. In one embodiment, microneedle patch 601, microneedles 602, compressed air container 605, suction pump 606, and/or flexible cap 608 are disposable as deemed necessary to maintain device sterility. In other embodiments, the entire microneedle-based component is disposable.

In one embodiment, the apparatus includes an additional energy source. The additional energy source is at least one of: an abrasive actuator, a mechanical motor, an electro-magnetic actuator, a piezoelectric transducer, a suction device, and a pressure device. In one embodiment, the additional energy source is configured for use in conjunction with the energy source to facilitate transfer of energy to the tissue. The additional energy source may be configured to provide energy to the tissue. The additional energy source may be configured to apply energy to the tissue either within the reservoir housing, or outside the reservoir housing. In another embodiment, the additional energy source is operatively connected to the tissue through the LPM in contact with the tissue. In another embodiment, the additional energy source comprises a pair of electrodes for application of electric current to the tissue.

In one embodiment, the energy source is configured to apply an optical energy to the tissue, and the optical energy is applied by a laser.

In one embodiment, the energy source is configured to be connected to an electrical source such as a battery, generator, or wall outlet. In another embodiment, the energy source is configured to be fluidly coupled to a source of LPM that may be provided as an element of an energy source or may be external to the energy source. In one embodiment, the LPM is used as a medium of energy, such as for example, in the use of ultrasound energy as an energy source. In another embodiment, any fluid, including a liquid or air, can be used as a medium of energy. In one embodiment, energy can be selectively applied to the tissue from only the energy source, from only the additional energy source, or from a combination thereof.

In one embodiment, the LPM can be manipulated before, during, and after application of the energy source to the tissue so as to reduce adverse thermal effects of energy exposure on the tissue or its constituents. In one embodiment, a pre-cooled LPM having a temperature lower than the ambient temperature is used for solubilization. In another embodiment, the temperature of the LPM is continuously reduced during energy application by transferring heat within the LPM to a pre-cooled liquid flowing through a heat-transfer jacket coupled to the sample container. In yet another embodiment, LPM is continuously circulated through the device to minimize elevation of LPM temperature prior to collection for analysis.

Sensor Mechanisms and Analysis

In one embodiment, the reservoir housing contains a diagnostic device, for example, an analyte sensor, for detecting and optionally quantifying analytes that may be present in the LPM. In one embodiment, the diagnostic device can be a chemical sensor and/or a biosensor, and/or can provide other measurements to form a complete sampling measurement system.

In another embodiment, the diagnostic device is located outside the reservoir housing, and the diagnostic device is configured to receive the contents of the reservoir housing. In one embodiment, the contents of the reservoir housing are transferred to the diagnostic device through pumping using mechanical forces, capillary forces, ultrasound, vacuum, or electrosonic forces.

In another embodiment, the diagnostic device is a portable disposable unit configured to receive solubilized tissue, either within or separate from the reservoir housing. In one embodiment, the diagnostic device and an energy source are operatively connected to the reservoir housing. The energy source may include electrical circuitry configured to measure tissue resistance and analyte concentration measurements, and display thereof. The energy source and diagnostic device may be operatively connected to the tissue of interest, upon which the energy source applies energy to the tissue, either alone or in combination with other physical, mechanical, electrical, and/or chemical forces. The tissue of interest may be solubilized, after which it may be collected in the disposable diagnostic device and analyzed using appropriate assays for point of care diagnostics. In another embodiment, the disposable diagnostic device may be transported to a laboratory for analysis.

In one embodiment, the apparatus may be integrated with a diagnostic probe, such as an endoscope, colonoscope, laparoscope, or any other diagnostic probe. In another embodiment, the apparatus includes a catheter.

Apparatus Applications

The apparatus is generally configured to solubilize tissue of interest. In one embodiment, the apparatus is configured to solubilize and collect a sample of a tissue of interest. In another embodiment, the apparatus is configured to detect any analyte present in a tissue of interest. In yet another embodiment, the apparatus is configured to perform diagnosis of a tissue of interest. In still another embodiment, the apparatus is configured to remove a tissue of interest, such as for example, a tumor, or other growth. In yet another embodiment, the apparatus is configured to perform treatment of a tissue of interest, such as for example acne treatment. In still another embodiment, the apparatus is configured to perform remodeling of a tissue of interest, such as for example remodeling of a nail.

In one embodiment, the tissue of interest is at least one of: surface tissue (e.g., skin), subsurface tissue (e.g., beneath a patient's skin), mucosal membrane, breast, prostate, eye, vagina, bladder, nail, hair, colon, testicles, intestine, lung, brain, pancreas, liver, heart, bone, aorta wall, tissue in situ, freshly resected tissue, frozen resected tissue, preserved paraffin embedded tissue, tissue and cell extracts and cultured cells, tissue hosting precancerous conditions, tumors, skin lesions, damaged skin, diseased tissue, inflammatory cells, thickened hyper-keratinized skin, malignant and benign growths and obstructions in the body or within the central and peripheral nervous systems, intra-abdominal and peritoneal adhesions, wounds including necrotic eschar and fibrinous slough, teeth, dentures, oral tissues, aged skin, scarred skin, UV-damaged skin, tattooed skin, acne, age spots, skin tags, seborrheic keratosis, scar tissue, adhesion, xanthomas, non-cancerous hyperproliferative conditions, surface bumps, scaly patches, skin discoloration, epithelial lesions due to chronic infections, warts, molluscum contagiosum, fungal diseases of the skin, fungal diseases of the nails, fungal diseases of the hair, fungal diseases of the mucous membranes, chronic skin lesion due to a microbial agent, superficial hemangiomas, intrasurgical hemostasis, and any other tissue.

In one embodiment, the apparatus is configured to deliver a drug to a tissue. The apparatus may include an energy source configured to be operatively connected to the tissue, a reservoir housing configured to be operatively connected to the tissue, LPM, and a drug. The apparatus is useful in assisting in the transport of a drug across at least one skin layer and into lower layers of skin, the bloodstream, or sub-dermal tissue. In one embodiment, the reservoir housing is configured to apply LPM and/or the drug to the tissue of interest. In one embodiment, the reservoir housing is configured to apply LPM to a tissue of interest causing solubilization of at least a portion thereof, after which a drug is applied to the tissue. In one embodiment, the reservoir housing is configured to collect and analyze a sample of the solubilized tissue. In another embodiment, the energy source is configured to apply energy to the tissue, wherein the energy source is any of the multiple energy sources described herein. In another embodiment, the LPM is configured to at least one of: couple an energy from the energy source to the tissue, facilitate solubilization of the tissue, store the drug to be delivered to the tissue, increase the solubility of the drug, and inhibit degradation of the drug. In one embodiment, the drug is stored within the reservoir housing prior to solubilization of the tissue. In another embodiment, the drug is stored outside the reservoir housing prior to solubilization of the tissue.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. An apparatus for solubilizing tissue, comprising:
a housing, comprising a vacuum chamber and a passage,
wherein the vacuum chamber comprises an outer wall, an inner wall, an upper wall, and an interior,
wherein the outer wall, the inner wall, and the upper wall define the interior, and wherein the inner wall is radially inward of the outer wall,
wherein the vacuum chamber is configured to selectively generate an air pressure within the interior that is less than ambient air pressure,
wherein the interior is configured to be operatively connected to the tissue,
wherein the passage is configured to be operatively connected to the tissue;
an energy source configured to be operatively connected to the tissue to apply energy to the tissue,
wherein the energy source is configured to access the tissue through the passage; and
a reservoir housing configured to contain a liquefaction promoting medium, the reservoir housing being operatively connected to apply the liquefaction promoting medium to the tissue,
the reservoir housing and the energy source being operatively connected to solubilize the tissue with the liquefaction promoting medium and the energy from the energy source.

2. The apparatus of claim 1, further comprising a port operatively connected to the vacuum chamber, wherein the port is configured to selectively allow at least one of introduction of a liquefaction promoting medium into the vacuum chamber and removal from the vacuum chamber of a liquefaction promoting medium containing solubilized tissue.

3. The apparatus of claim 1, further comprising a port operatively connected to the passage, wherein the port is configured to selectively allow at least one of introduction of liquefaction promoting medium into the passage and removal from the vacuum chamber of a liquefaction promoting medium containing solubilized tissue.

4. The apparatus of claim 1, further comprising a sample container, at least a portion of which is positioned within at least a portion of the passage.

5. The apparatus of claim 4, further comprising a port operatively connected to the sample container, wherein the port is configured to at least one of: selectively allow introduction of liquefaction promoting medium into the vacuum chamber and removal from the vacuum chamber of a liquefaction promoting medium containing solubilized tissue.

6. The apparatus of claim 1, wherein the energy source is configured to apply the energy as a mechanical energy to the tissue.

7. The apparatus of claim 1, wherein the energy source comprises an abrasive component connected to a shaft, and wherein the abrasive component is at least one of: a sheet of abrasive material, an abrasive disc, an abrasive ring, and a brush having bristles.

8. The apparatus of claim 1, wherein at least a portion of the outer wall is flexible and biased toward a radially outward direction, and wherein at least a portion of the outer wall is configured to be selectively displaced radially inwardly and released, resulting in the generation of an air pressure within the interior that is less than ambient air pressure.

* * * * *